(12) United States Patent
Bajema et al.

(10) Patent No.: US 11,458,286 B2
(45) Date of Patent: Oct. 4, 2022

(54) CATHETER STRUCTURES FOR REDUCING FLUOROSCOPY USAGE DURING ENDOVASCULAR PROCEDURES

(71) Applicant: CLEARSTREAM TECHNOLOGIES LIMITED, Enniscorth (IE)

(72) Inventors: Nicholas Loren Bajema, Phoenix, AZ (US); Jim C. Beasley, Phoenix, AZ (US); Kevin Boyle, Scottsdale, AZ (US); Alexander William Tessmer, Phoenix, AZ (US); Mark Nicholas Wright, Gilbert, AZ (US)

(73) Assignee: CLEARSTREAM TECHNOLOGIES LIMITED, Enniscorthy (IE)

( * ) Notice: Subject to any disclaimer, the term of this patent is extended or adjusted under 35 U.S.C. 154(b) by 1464 days.

(21) Appl. No.: 15/301,141

(22) PCT Filed: Mar. 31, 2015

(86) PCT No.: PCT/US2015/023574
§ 371 (c)(1),
(2) Date: Sep. 30, 2016

(87) PCT Pub. No.: WO2015/153599
PCT Pub. Date: Oct. 8, 2015

(65) Prior Publication Data
US 2017/0021139 A1    Jan. 26, 2017

Related U.S. Application Data

(60) Provisional application No. 62/083,745, filed on Nov. 24, 2014, provisional application No. 61/972,580, filed on Mar. 31, 2014.

(51) Int. Cl.
*A61B 17/3207*    (2006.01)
*A61M 25/09*    (2006.01)
(Continued)

(52) U.S. Cl.
CPC ......... *A61M 25/09* (2013.01); *A61B 17/3207* (2013.01); *A61M 25/01* (2013.01);
(Continued)

(58) Field of Classification Search
CPC ...... A61M 25/09; A61M 25/01; A61M 25/10; A61M 25/104; A61M 2025/0008; A61M 2025/1079; A61F 2250/0097
See application file for complete search history.

(56) References Cited

U.S. PATENT DOCUMENTS 550,238 A    11/1895    Allen, Jr.
4,133,303 A    1/1979    Patel
(Continued)

FOREIGN PATENT DOCUMENTS

CA    2635157 A1    12/2009
CN    201223627 Y    4/2009
(Continued)

OTHER PUBLICATIONS

Clinical Research Studies; From the Society for Vascular Surgery; Journal of Vascular Surgery pp. 886-894e1; Apr. 2011; Comparison of indirect radiation dose estimates with directly measured radiation dose for patients and operators during complex endovascular procedures; Giuseppe Panuccio, MD, Roy K. Greenberg, MD, Kevin Wunderle, MSc, Tara M. Mastracci, MD, Matthew G. Eagleton, MD, and William Davros, PhD; Cleveland, Ohio.
(Continued)

*Primary Examiner* — Bhisma Mehta
*Assistant Examiner* — William R Frehe
(74) *Attorney, Agent, or Firm* — Dickinson Wright PLLC; Andrew D. Dorisio

(57) ABSTRACT

A catheter structure, such as a balloon catheter (30), guidewire, or the like, with markings (32) perceptible outside of the vasculature is for use in determining at a location
(Continued)

external to the body the position of the catheter structure relative to a treatment area. Related kits are also disclosed.

9 Claims, 12 Drawing Sheets

(51) Int. Cl.
| | |
|---|---|
| *A61M 25/10* | (2013.01) |
| *A61M 25/01* | (2006.01) |
| *A61M 25/00* | (2006.01) |
| *A61F 2/958* | (2013.01) |
| *A61B 90/00* | (2016.01) |
| *A61B 17/22* | (2006.01) |

(52) U.S. Cl.
CPC .......... *A61M 25/10* (2013.01); *A61M 25/104* (2013.01); *A61B 17/22* (2013.01); *A61B 2017/22051* (2013.01); *A61B 2090/062* (2016.02); *A61F 2/958* (2013.01); *A61F 2250/0097* (2013.01); *A61M 2025/0008* (2013.01); *A61M 2025/0183* (2013.01); *A61M 2025/1079* (2013.01)

(56) References Cited

U.S. PATENT DOCUMENTS

| | | | |
|---|---|---|---|
| 4,464,175 A | 8/1984 | Altman et al. | |
| 4,776,347 A | 10/1988 | Matthews | |
| 4,981,470 A | 1/1991 | Bombeck, IV | |
| 5,021,043 A | 6/1991 | Becker et al. | |
| 5,030,227 A | 7/1991 | Rosenbluth et al. | |
| 5,109,869 A | 5/1992 | Buckley | |
| 5,114,401 A * | 5/1992 | Stuart | A61M 25/09 604/161 |
| 5,163,927 A | 11/1992 | Woker et al. | |
| 5,209,730 A | 5/1993 | Sullivan | |
| 5,324,269 A | 6/1994 | Miraki | |
| 5,437,290 A | 8/1995 | Bolger et al. | |
| 5,591,128 A | 1/1997 | Sithole | |
| 5,657,764 A | 8/1997 | Coulter et al. | |
| 5,709,661 A | 1/1998 | Van Egmond et al. | |
| 5,836,895 A | 11/1998 | Ramsey, III | |
| 5,851,210 A | 12/1998 | Torossian | |
| 5,860,923 A | 1/1999 | Lenker et al. | |
| 5,864,961 A | 2/1999 | Vaughan | |
| 6,074,367 A | 6/2000 | Hubbell | |
| 6,078,832 A | 6/2000 | Lenker et al. | |
| 6,143,016 A | 11/2000 | Bleam et al. | |
| 6,210,338 B1 | 4/2001 | Afremov et al. | |
| 6,241,678 B1 | 6/2001 | Afremov et al. | |
| 6,264,633 B1 | 7/2001 | Knorig | |
| 6,273,895 B1 | 8/2001 | Pinchuk et al. | |
| 6,494,848 B1 | 12/2002 | Sommercorn et al. | |
| 6,575,932 B1 | 6/2003 | O'Brien et al. | |
| 6,620,114 B2 | 9/2003 | Vrba et al. | |
| 6,645,233 B1 | 11/2003 | Ayers et al. | |
| 6,884,257 B1 | 4/2005 | Cox | |
| 7,011,654 B2 | 3/2006 | Dubrul et al. | |
| 7,022,103 B2 | 4/2006 | Cappiello et al. | |
| 7,048,698 B2 | 5/2006 | Whalen et al. | |
| 7,211,110 B2 | 5/2007 | Rowe et al. | |
| 7,520,876 B2 | 4/2009 | Ressemann et al. | |
| 7,549,997 B2 | 6/2009 | Davis, Jr. et al. | |
| 7,828,793 B2 | 11/2010 | Thompson et al. | |
| 7,837,677 B2 | 11/2010 | Thompson et al. | |
| 7,867,271 B2 | 1/2011 | Geiser et al. | |
| 8,043,285 B2 | 10/2011 | Thompson et al. | |
| 8,080,031 B2 | 12/2011 | Isham | |
| 8,083,692 B2 | 12/2011 | Mangiardi et al. | |
| 8,114,113 B2 | 2/2012 | Becker | |
| 8,512,389 B2 | 8/2013 | Ayala et al. | |
| 8,556,851 B2 | 10/2013 | Hirszowicz et al. | |
| 9,084,558 B2 | 7/2015 | Furbush, Jr. | |
| 9,205,213 B2 | 12/2015 | Mythen | |
| 9,232,914 B2 | 1/2016 | Notter | |
| 2003/0083594 A1 | 5/2003 | Sommercorn et al. | |
| 2003/0135086 A1* | 7/2003 | Khaw | A61M 1/1024 600/16 |
| 2004/0068190 A1 | 4/2004 | Cespedes | |
| 2004/0253185 A1 | 12/2004 | Herweck et al. | |
| 2006/0015039 A1 | 1/2006 | Cassidy et al. | |
| 2006/0052766 A1 | 3/2006 | Patel | |
| 2006/0116658 A1 | 6/2006 | McMichael et al. | |
| 2007/0060879 A1 | 3/2007 | Weitzner et al. | |
| 2007/0073269 A1 | 3/2007 | Becker | |
| 2007/0106213 A1 | 5/2007 | Spera et al. | |
| 2008/0045896 A1 | 2/2008 | Yribarren et al. | |
| 2008/0188803 A1 | 8/2008 | Jang | |
| 2008/0255475 A1* | 10/2008 | Kondrosky | A61M 25/09 600/585 |
| 2008/0269643 A1 | 10/2008 | Morriss | |
| 2009/0054760 A1 | 2/2009 | Burke | |
| 2009/0131785 A1 | 5/2009 | Lee et al. | |
| 2011/0004057 A1 | 1/2011 | Goldfarb et al. | |
| 2011/0060275 A1 | 3/2011 | Christiansen | |
| 2011/0098684 A1 | 4/2011 | Trubiano | |
| 2012/0010646 A1 | 1/2012 | Keith et al. | |
| 2012/0316589 A1* | 12/2012 | Schaeffer | A61M 25/104 606/170 |
| 2013/0281971 A1 | 10/2013 | Looper et al. | |
| 2014/0007956 A1* | 1/2014 | Rutty | A61M 25/10 137/551 |
| 2015/0032118 A1 | 1/2015 | Okamura et al. | |
| 2015/0045649 A1 | 2/2015 | O'Dea et al. | |
| 2015/0099935 A1 | 4/2015 | Runnels | |
| 2015/0148601 A1* | 5/2015 | Weiner | A61M 25/0105 600/109 |
| 2015/0335860 A1* | 11/2015 | Klocke | A61M 25/0108 604/510 |
| 2015/0335866 A1* | 11/2015 | Stapleton | A61M 25/10 604/103.02 |
| 2016/0045218 A1 | 2/2016 | Swisher et al. | |
| 2017/0043142 A1* | 2/2017 | Bareau | A61B 1/00082 |

FOREIGN PATENT DOCUMENTS

| | | |
|---|---|---|
| CN | 201519356 U | 7/2010 |
| CN | 201840763 U | 5/2011 |
| CN | 103282075 A | 9/2013 |
| EP | 0087220 B1 | 8/1983 |
| EP | 1601406 B1 | 9/2004 |
| GB | 2355797 A | 5/2001 |
| JP | H10323386 A | 12/1998 |
| JP | H11128353 A | 5/1999 |
| JP | 2003275323 A | 9/2003 |
| JP | 2007020885 A | 2/2007 |
| JP | 2010524581 A | 7/2010 |
| WO | WO0172221 A1 | 10/2001 |
| WO | 2008007350 A1 | 1/2008 |
| WO | 2008033929 A2 | 3/2008 |
| WO | 2008091652 A2 | 7/2008 |
| WO | WO2008131017 A2 | 10/2008 |
| WO | 2014018659 A2 | 1/2014 |

OTHER PUBLICATIONS

Radiation exposure to operating room personnel and patients during endovascular procedures; Abhisekh Mohapatra, BA, Roy K. Greenberg, MD, Tara M. Mastracci, MD, Matthew J. Eagleton, MD, and Brett Thornsberry, RT(R) Cleveland, Ohio; Journal of Vascular Surgery Sep. 2013, vol. 58, No. 3; pp. 702-709.

Patient radiation exposure during percutaneous endovascular revascularization of the lower extremity Einat Segal, MD, Ido Weinberg, MD, MSc, Isaac Leichter, PhD, Alexander Klimov, MD, Jay Giri, MD, MPH, and Allan I. Bloom, MD; Jerusalem, Israel; Boston, Mass; and Philadelphia, Pa; Journal of Vascular Surgery; vol. 58, No. 6; Dec. 2013; pp. 1556-1562.

Controlling Radiation Exposure in Interventional Cardiology; Editor's Perspective; J. Dawn Abbott, MD Circ Cardiovasc Interv Aug. 2014 pp. 426-428.

(56) References Cited

OTHER PUBLICATIONS

From the Southern Association for Vascular Surgery; Radiation-induced skin injury after complex endovascular procedures; Melissa L. Kirkwood, MD, Gary M. Arbique, PhD, Jeffrey B. Guild, PhD, Carlos Timaran, MD, R. James Valentine, MD and Jon A. Anderson, PhD, Dallas, Tex Journal of Vascular Surgery; vol. 60, No. 3; pp. 742-748; Sep. 2014.
Mini-Focus Issue:Radiation Dose Reduction; Clinical Research; Radiation Dose Reduction in the Cardiac Catheterization Laboratory Utilizing a Novel Protocol; Anthony W. A. Wassef, MD, et al.; Winnipeg, Manitoba, Canada; JACC: Cardiovascular Interventions; vol. 7, No. 5, 2014 © 2 0 1 4 by the American College of Cardiology Foundation ISSN 1936-8798 Published by Elsevier Inc. http://dx.doi.org/10.1016/j.cin.2013.11.022.
English Machine Translation of CN103282075A.
English Machine Translation of CN201223627Y.
www.dictionary.com, dated Oct. 28, 2016, definition for angioplasty, attached as pdf.
English Machine Abstract for JPH10323386A dated Dec. 8, 1998.
English Machine Abstract for JP2003275323A dated Sep. 30, 2003.

\* cited by examiner

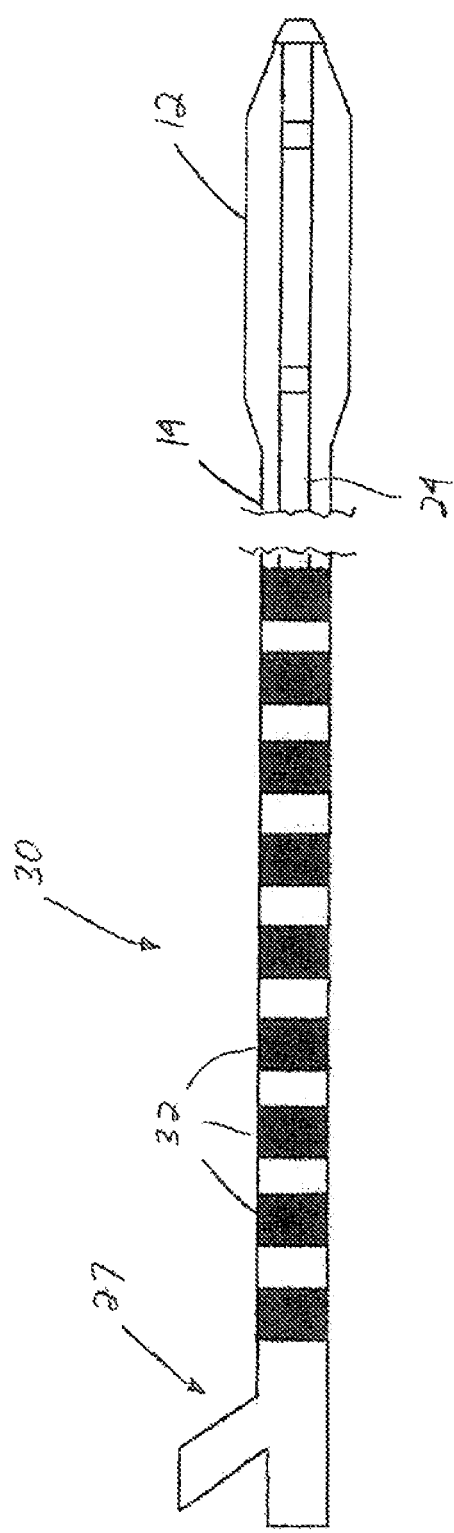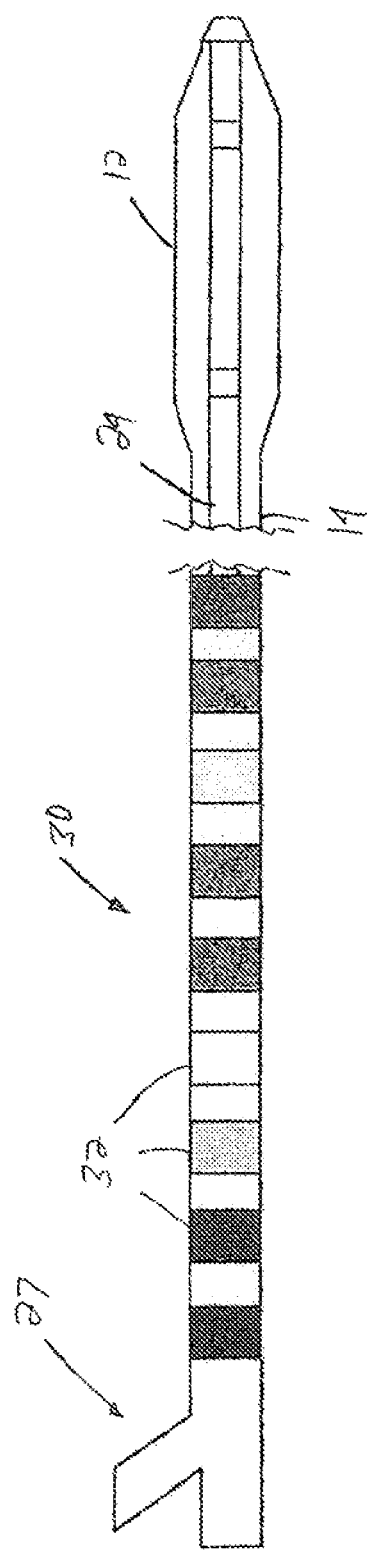

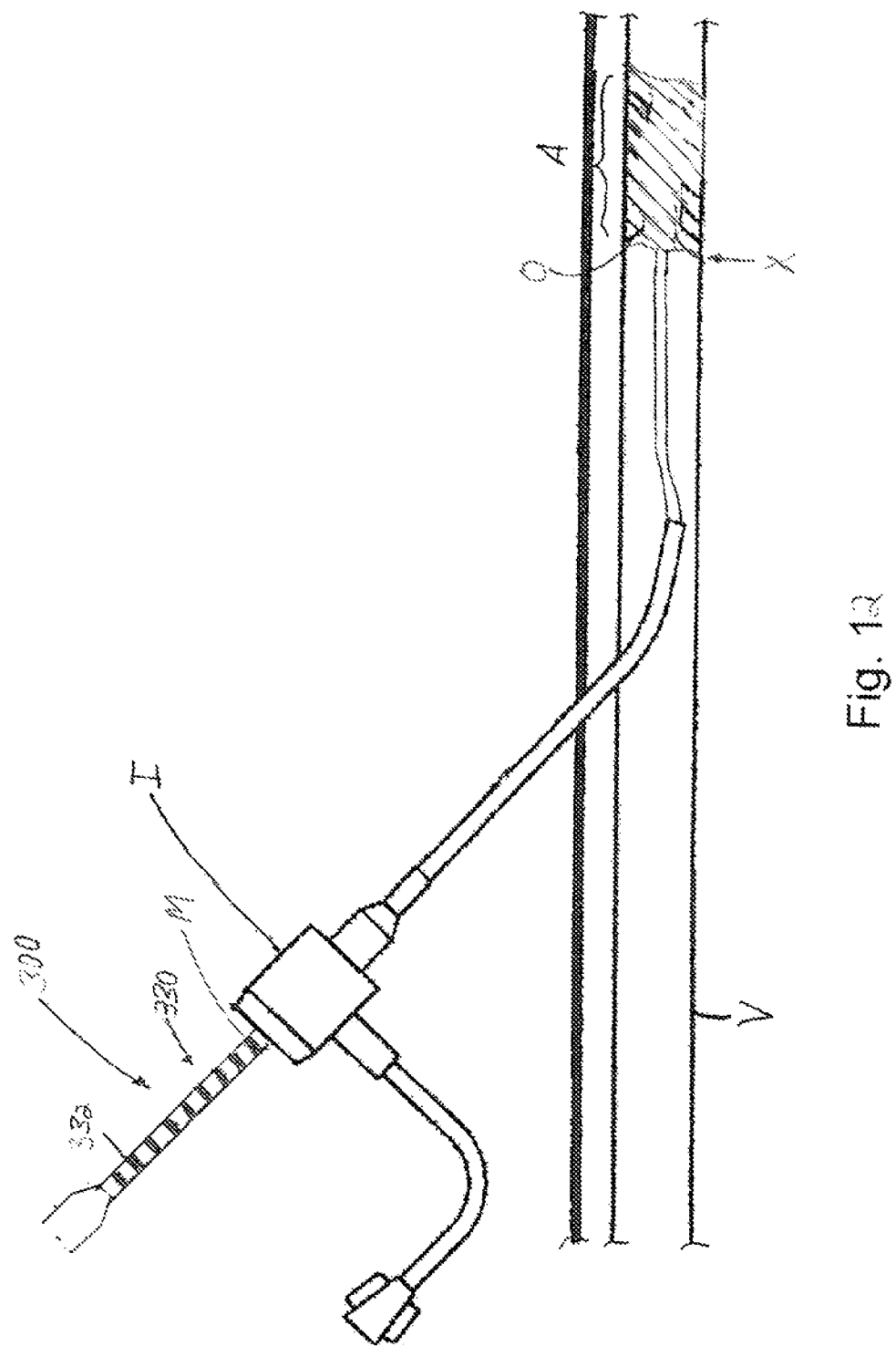

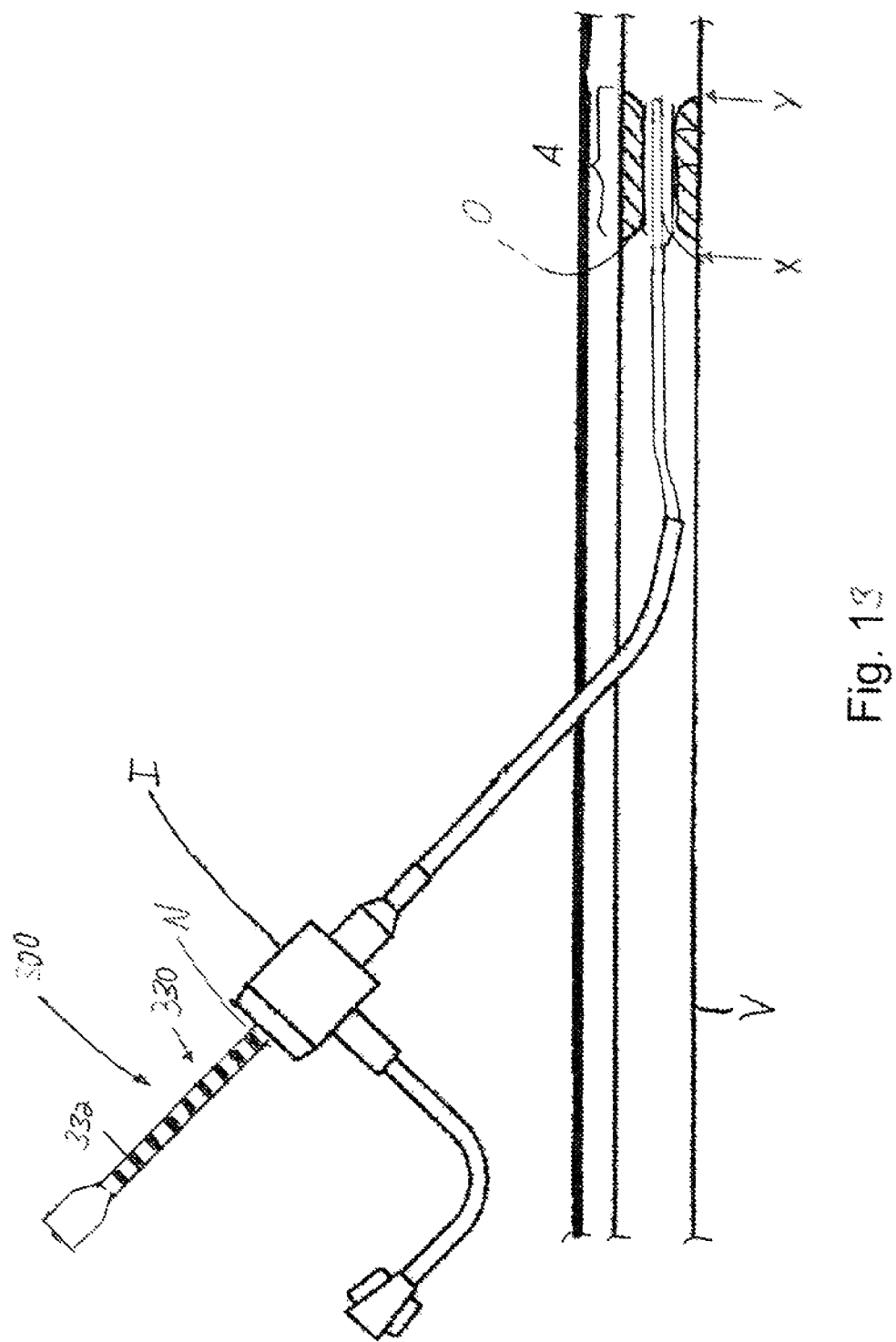

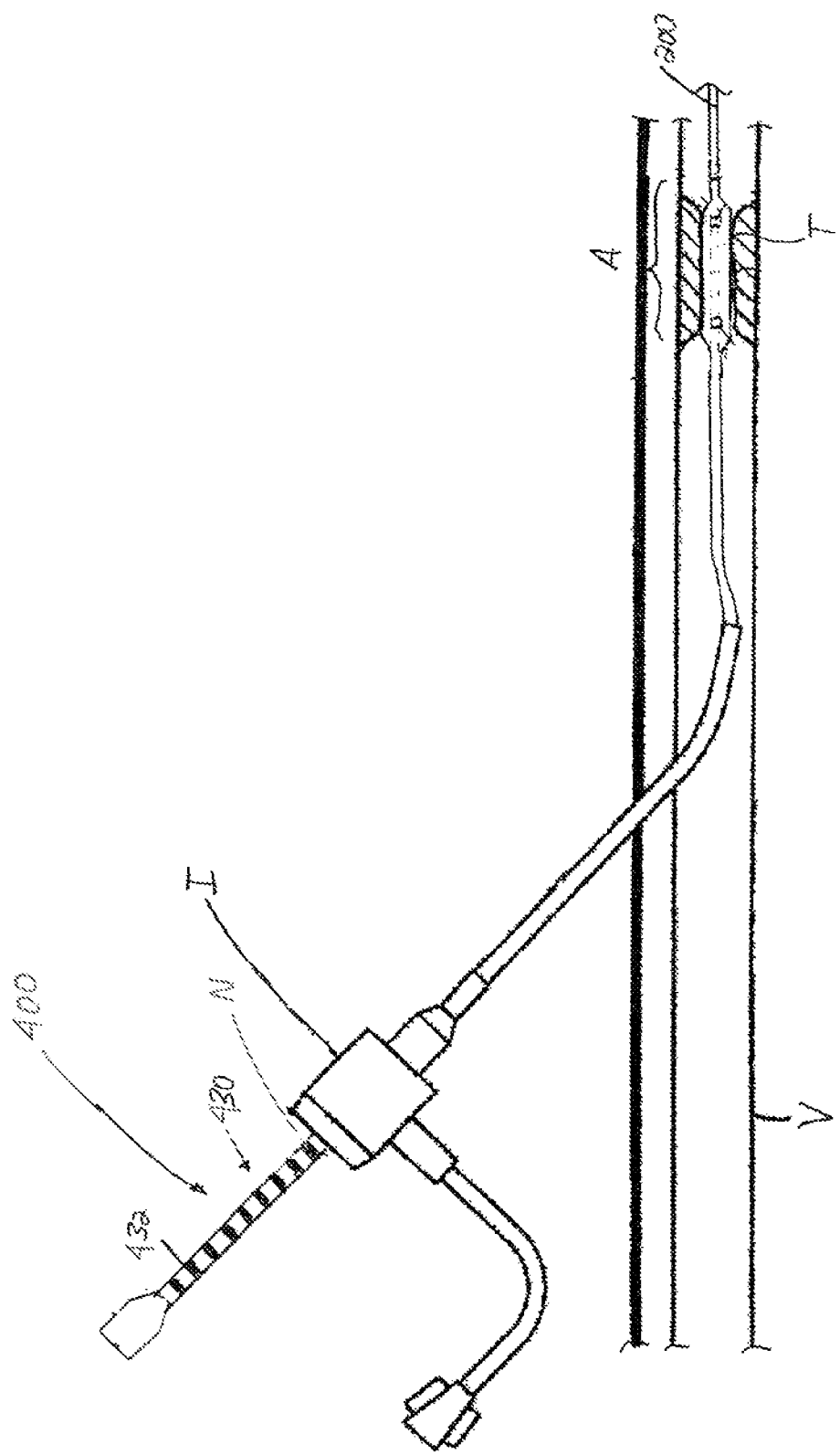

CATHETER STRUCTURES FOR REDUCING FLUOROSCOPY USAGE DURING ENDOVASCULAR PROCEDURES

This application claims priority to U.S. Provisional Patent Application Ser. Nos. 61/972,580, filed Mar. 31, 2014, and 62/083,745, filed Nov. 24, 2014, the disclosures of which are incorporated by reference.

TECHNICAL FIELD

This disclosure relates generally to interventional medical procedures, such as angioplasty, and, more particularly, to a catheter structure with markings to reduce the usage of fluoroscopy during the procedure.

BACKGROUND

A clinician performing an endovascular procedure, such as angioplasty, will typically use fluoroscopy in the course of performing a diagnostic angiogram to assess the location of a treatment area (such as where a lesion or blockage is present in the vasculature). Upon gaining guidewire access to the vasculature using additional fluoroscopy, and then inserting the catheter along the guidewire, the clinician will then typically use even more fluoroscopy, either continuously or intermittently (e.g., "spot checking"), in order to confirm the catheter has reached the location of the treatment area. As can be appreciated, this conventional approach increases the exposure of the patient and others, including the clinician and assistants, to fluoroscopy and, hence, radiation, which is generally desired to be avoided to the greatest extent possible.

Accordingly, a need exists for a manner in which to position a catheter structure into the vasculature at a treatment area while reducing the amount or frequency of fluoroscopy used.

SUMMARY

One object of the disclosure is to provide a catheter structure, such as a balloon catheter, guidewire, or the like, with markings perceptible outside of the vasculature for use in determining at a location external to the body the position of the catheter structure relative to a treatment area.

One embodiment relates to an apparatus for use by a clinician in treating the vasculature. The apparatus may include a catheter structure having a shaft including a first distal portion adapted for positioning at the treatment area and a proximal portion including a marking perceptible by the clinician external to the vasculature without the use of fluoroscopy, the marking being representative of a length from a pre-determined starting point on the catheter structure. Consequently, the markings may be used to position the catheter structure a distance in the vasculature corresponding to the length with minimal use of fluoroscopy.

The marking may comprise a plurality of regularly spaced marks or irregularly spaced marks. In one aspect, the marking may be printed on the catheter structure. The markings may comprise a plurality of first marks and at least one second mark different from the plurality of first marks. For example, the first marks may comprise spaced bands and the second mark may comprise an alphanumerical indicia. The marking may be provided adjacent a hub associated with the catheter structure. In a further aspect, the marking may be luminescent, such as chemiluminescent or photoluminescent.

In a further aspect, the catheter structure may comprise a balloon adjacent to a tip including the pre-determined starting point. One or more radiopaque markings may be adjacent to the balloon.

The catheter structure may include a treatment element selected from the group consisting of a drug, a stent, a graft, a cutter, a focused force wire, or any combination thereof. Additionally, the catheter structure may comprise a guidewire, and may be adapted for slidably receiving the guidewire.

In another embodiment, an apparatus for treating a treatment area at an intravascular location in a body is disclosed. The apparatus may include a catheter including a shaft having a distal portion including a balloon and a proximal portion including at least one marking arranged for being viewed at a reference point external to the body for identifying a distance from the treatment area to the reference point. The balloon may further include a treatment element selected from the group consisting of a stent, a graft, a cutter, a focused force wire, or any combination thereof.

Another embodiment relates to a method of treating a treatment area in a body. The method may comprise inserting a distal portion of a guidewire to the treatment area, determining a position of a first marking on a proximal portion of the guidewire relative to a reference point, and inserting a catheter a distance corresponding to the first marking.

A further embodiment relates to an apparatus for use by a clinician in treating the vasculature. The apparatus may include a catheter structure having a shaft including a first distal portion adapted for positioning at the treatment area and a proximal portion, and means external to the vasculature for determining a length from a pre-determined starting point on the catheter structure, whereby the determining means may be used to position the catheter structure a distance in the vasculature corresponding to the length with minimal use of fluoroscopy.

Another embodiment comprises a catheter including a ruler. A further embodiment comprises a guidewire including a ruler. A catheter comprising a ruler may be provided and/or used in combination with a guidewire comprising a ruler.

In another embodiment, a crossing catheter is provided including a plurality of markings for determining a distance of insertion into a patient's vasculature. The plurality of markings may comprise a ruler.

An additional embodiment relates to a method of forming a catheter structure. The method may comprise comprising providing a marking perceptible to a clinician on a first portion of the catheter structure external to the vasculature to provide a representation of an amount a second portion of the catheter structure has been inserted into the vasculature. The providing step may comprise printing the marking on the catheter structure. The providing step may further comprise providing a plurality of first marks and at least one second mark different from the plurality of first marks. The first marks may comprise spaced bands and the second mark may comprise an alphanumerical indicia. In one aspect, the amount represents a total distance the second portion of the catheter structure has been inserted into the vasculature from a reference point external to the vasculature.

Any of the catheters and/or guidewires disclosed herein may be provided together in a kit for the treatment of a treatment area in a patient's vasculature. For example, one embodiment relates to a kit for treating a treatment area in the vasculature. The kit may include a first crossing catheter having a first shaft including a first distal portion adapted for positioning at or near the treatment area and a first proximal portion including a first marking at a first location, and a second catheter having a second shaft including a second distal portion adapted for positioning at the treatment area and a second proximal portion including a second marking at a second location substantially matching a first location of the first marking. The crossing catheter may be adapted for penetrating into or through an occlusion at the treatment area.

A further embodiment includes a kit for treating a treatment area in the vasculature. The kit may comprise a first crossing catheter having a first shaft including a first distal portion adapted for positioning at or near the treatment area and a first proximal portion including a first marking at a first location corresponding to a first margin of the treatment area and a second marking at a second location corresponding to a second margin of the treatment area, as well as a second catheter having a second shaft including a second distal portion adapted for positioning at the treatment area and a second proximal portion including a third marking at a third location substantially matching the first location or the second location on the first, crossing catheter. The second catheter may further include a fourth marking on the second proximal portion at a fourth location corresponding to the other of the first location or the second location on the first, crossing catheter. The second catheter may also include a technology selected from the group consisting of an artherectomy technology, a thrombectomy technology, a PTA technology, a stent technology, and any combination of the foregoing.

In addition, a method of treating a treatment area in a body is disclosed. The method may include inserting a crossing catheter to at least a proximal portion of the treatment area, determining a position of a first marking on the crossing catheter, and inserting a second catheter at least a distance corresponding to the first marking. The method may further include the steps of, after the determining step, inserting the crossing catheter to a distal portion of the treatment area, and determining a position of a second marking on the crossing catheter. The step of inserting the crossing catheter to the distal portion of the treatment area may comprise passing the crossing catheter through an occlusion. In one aspect, the crossing catheter may be adapted to penetrate into an occlusion or the occlusion at the treatment area. The crossing catheter may be adapted to apply energy for penetrating into the occlusion or the occlusion. For example, the crossing catheter may comprise a cutter, a vibrator, a source of light, a source of fluid, a nozzle, a rigid or tapered distal tip, or any combination of the foregoing.

A further embodiment relates to a kit for treating a treatment area in the vasculature of a patient. The kit of this embodiment may comprise a first crossing catheter having a first shaft including a first distal portion adapted for positioning at or near the treatment area and a first proximal portion including a first marking at a first location, and a second catheter having a second shaft including a second distal portion adapted for positioning at the treatment area and a second proximal portion including a second marking at a second location substantially matching a first location of the first marking. Each of the first marking and the second marking may be visible external to the patient's body without the use of fluoroscopy. In one aspect, the second distal portion of the second catheter comprises a balloon. The second catheter may comprise a treatment element selected from the group consisting of a drug, a stent, a graft, a cutter, a focused force wire, or any combination thereof.

Furthermore, the crossing catheter may be adapted for penetrating into or through an occlusion at the treatment area.

Another embodiment relates to a kit for treating a treatment area in the vasculature, comprising a first crossing catheter having a first shaft including a first distal portion adapted for positioning at or near the treatment area and a first proximal portion including a first marking at a first location corresponding to a first margin of the treatment area and a second marking at a second location corresponding to a second margin of the treatment area, and a second catheter having a second shaft including a second distal portion adapted for positioning at the treatment area and a second proximal portion including a third marking at a third location substantially matching the first location or the second location on the first, crossing catheter. The second catheter may further include a fourth marking on the second proximal portion at a fourth location corresponding to the other of the first location or the second location on the first, crossing catheter. In one aspect, the second catheter may include a technology selected from the group consisting of an artherectomy technology, a thrombectomy technology, a PTA technology, a stent technology, and any combination of the foregoing. In any of the above embodiments, the crossing catheter may be adapted to penetrate into an occlusion or the occlusion at the treatment area. The crossing catheter may be adapted to apply energy for penetrating into an occlusion or the occlusion. In a further aspect, the crossing catheter comprises a cutter, a vibrator, a source of light, a source of fluid, a nozzle, a rigid or tapered distal tip, or any combination of the foregoing.

In still a further embodiment, a kit is disclosed for treating a treatment area in a vasculature of a patient. The kit of this further embodiment may comprise a first crossing catheter having a first shaft including a first distal portion adapted for positioning at the treatment area and a first proximal portion including a plurality of first markings perceptible by the clinician external to the vasculature without the use of fluoroscopy, each of the plurality of first markings being representative of a length from a first predetermined starting point on the first crossing catheter, and a second catheter having a second shaft including a second distal portion adapted for positioning at the treatment area and a second proximal portion including a plurality of second markings perceptible by the clinician external to the vasculature without the use of fluoroscopy, each of the plurality of second markings being representative of a length from a second predetermined starting point of the second catheter, wherein a distance between the first predetermined starting point and each of the first markings corresponds to a distance between the second predetermined starting point and each of the second markings.

In this embodiment, the plurality of first markings may be spaced at regular intervals from one another. Each of the first shaft and the second shaft may further include alphanumeric markings corresponding to each of the first markings and the second markings. At least one of the first markings or the second markings may be chemiluminescent or photoluminescent. In one aspect, at least one of the first markings or the second markings comprises spaced bands.

The second catheter may comprise a balloon adjacent a tip including the second predetermined starting point. In addition, a radiopaque marker may be adjacent the balloon.

In another embodiment, a kit for treating a treatment area in a vasculature of a patient is disclosed. The kit comprises a first crossing catheter having a first shaft including a first distal portion adapted for positioning at the treatment area and a first proximal portion including a first ruler thereon. The first ruler may be perceptible by the clinician external to the vasculature without the use of fluoroscopy for measuring a distance from a first predetermined starting point on the first crossing catheter. A second catheter having a second shaft including a second distal portion adapted is for positioning at the treatment area and a second proximal portion including a second ruler thereon. The second ruler is also perceptible by the clinician external to the vasculature without the use of fluoroscopy for measuring a distance from a second predetermined starting point of the second catheter.

A further embodiment relates to a kit for treating a treatment area in a vasculature of a patient comprising a first crossing catheter having a first shaft including first means for measuring a plurality of first distances from a first predetermined point on the first shaft, and a second catheter having a second shaft including second means for measuring a plurality of second distances from a second predetermined point on the second shaft, wherein the first means for measuring and the second means for measuring are perceptible by the clinician external to the vasculature without the use of fluoroscopy (and may, for example, be non-radiopaque in nature), and wherein each of the plurality of first distances corresponds to at least one of the plurality of second distances. The second catheter may comprise a balloon adjacent a distal end of the second shaft, and wherein the second predetermined point may be an end of the balloon. The second catheter may further comprise a radiopaque marker adjacent the balloon.

An additional embodiment is a kit for treating a treatment area in a vasculature of a patient. The kit comprises a guidewire having a first distal portion adapted for positioning at or near the treatment area and a first proximal portion including a plurality of first markings perceptible by the clinician external to the vasculature without the use of fluoroscopy, each of the plurality of first markings being representative of a length from a first predetermined starting point on the catheter, and a catheter having a shaft including second distal portion adapted for positioning at the treatment area and a second proximal portion including a plurality of second markings perceptible by the clinician external to the vasculature without the use of fluoroscopy, each of the plurality of second markings being representative of a length from a second predetermined starting point of the second catheter, wherein a distance between the first predetermined starting point and each of the first markings corresponds to a distance between the second predetermined starting point and each of the second markings.

The catheter may comprise a balloon. In one aspect, the balloon may be located at a distal end of the catheter, and the second predetermined starting point may be located at a proximal end or a distal end of the balloon. In addition, a radiopaque marker may be adjacent the balloon.

The kit may also be provided such that the catheter comprises a treatment element selected from the group consisting of a drug, a stent, a graft, a cutter, a focused force wire, or any combination thereof. The catheter may include a technology selected from the group consisting of an artherectomy technology, a thrombectomy technology, a PTA technology, a stent technology, and any combination of the foregoing.

In one aspect, the plurality of first markings are spaced at regular intervals from one another.

The guidewire and the catheter may further include alphanumeric markings corresponding to each of the first markings and the second markings. At least one of the first markings or the second markings may be chemiluminescent or photoluminescent. In another aspect, at least one of the first markings or the second markings may comprise spaced bands.

As disclosed in another embodiment, a kit for treating a treatment area in a vasculature of a patient comprises a guidewire including a first distal portion adapted for positioning at the treatment area and a first proximal portion including a first ruler thereon. The first ruler is perceptible by the clinician external to the vasculature without the use of fluoroscopy, and may be non-radiopaque. The first ruler may be adapted for measuring a distance from a first predetermined starting point on the guidewire, and a catheter having a shaft including a second distal portion adapted for positioning at the treatment area and a second proximal portion including a second ruler thereon. The second ruler may be perceptible by the clinician external to the vasculature without the use of fluoroscopy, such as for example, being non-radiopaque. The second ruler may be adapted for measuring a distance from a second predetermined starting point of the catheter.

A still further embodiment relates to a kit for treating a treatment area in a vasculature of a patient. The kit comprises a guidewire including first means for measuring a plurality of first distances from a first predetermined point on the guidewire, and a catheter including second means for measuring a plurality of second distances from a second predetermined point on the catheter. The first means for measuring and the second means for measuring may be non-radiopaque in nature and are perceptible by the clinician external to the vasculature without the use of fluoroscopy. Each of the plurality of first distances may correspond (e.g., be equal to) at least one of the plurality of second distances. The catheter may comprise a balloon adjacent a distal end of the catheter, and the second predetermined point may be an end of the balloon. The catheter may further comprise a radiopaque marker adjacent the balloon.

In another embodiment, a device for treating a treatment area in the vasculature of a patient is disclosed, said device comprising a crossing catheter having a shaft including a distal portion adapted for positioning at or near the treatment area and a proximal portion including a plurality of markings, said markings being visible external to the patient's body without the use of fluoroscopy.

In one aspect, the plurality of markings may comprise a first marking at a first location corresponding to a first margin of the treatment area and a second marking at a second location corresponding to a second margin of the treatment area.

In another aspect, each of the plurality of markings may be representative of at least one known length from a predetermined starting point on the crossing catheter. These plurality of markings may be spaced at regular intervals from one another. The shaft may additionally include alphanumeric markings corresponding to each of the plurality of markings.

In any of the above embodiments, at least one of the markings may be chemiluminescent or photoluminescent. Furthermore, at least one of the markings may comprise a spaced band.

In a further embodiment, a device for treating a treatment area in a vasculature of a patient is disclosed, said device comprising a crossing catheter having a shaft including a distal portion adapted for positioning at the treatment area and a proximal portion including a ruler thereon, said ruler being perceptible by the clinician external to the vasculature without the use of fluoroscopy for measuring a distance from a predetermined starting point on the crossing catheter.

In any of the above embodiments, the crossing catheter may be adapted for penetrating into or through an occlusion at the treatment area.

In any of the above embodiments, a marking perceptible by the clinician external to the vasculature without the use of fluoroscopy may be a non-radiopaque marking.

BRIEF DESCRIPTION OF THE DRAWINGS

FIG. 5 and FIG. 6 show details of a catheter structure according to an embodiment of the present disclosure.

FIG. 12, FIG. 13, and FIG. 14 show one way of using a marked crossing catheter in combination with another catheter according to a further embodiment.

DETAILED DESCRIPTION

The description provided below and in regard to the figures applies to all embodiments unless noted otherwise, and features common to each embodiment are similarly shown and numbered.

Figure 1:
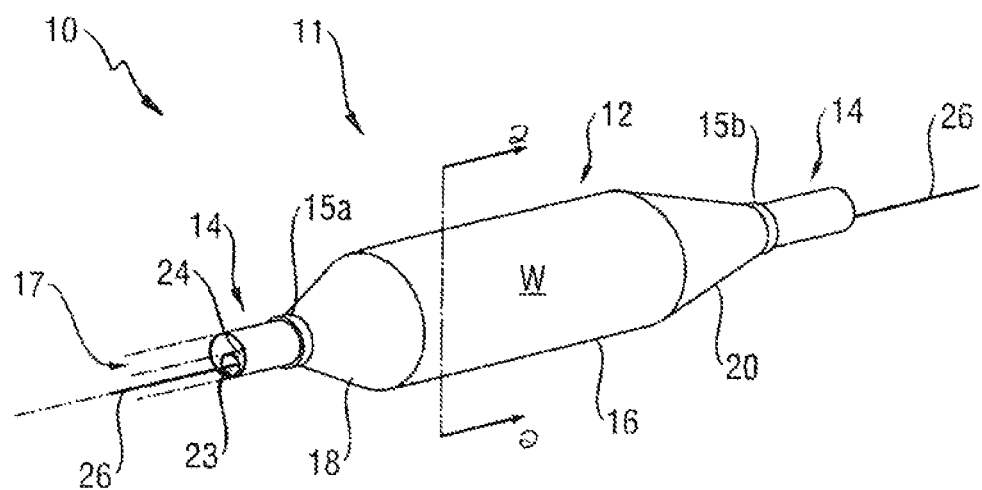
FIG. 1 is a perspective view of a catheter and balloon according to an embodiment disclosed herein.
Figure 2:
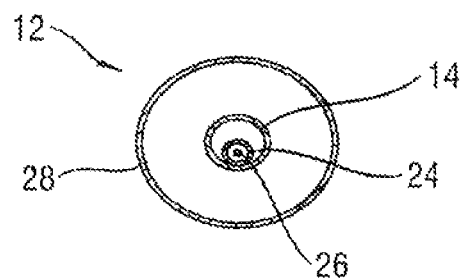
FIG. 2 is a cross-section of the balloon of FIG. 1 along line 2-2.
Figure 3:
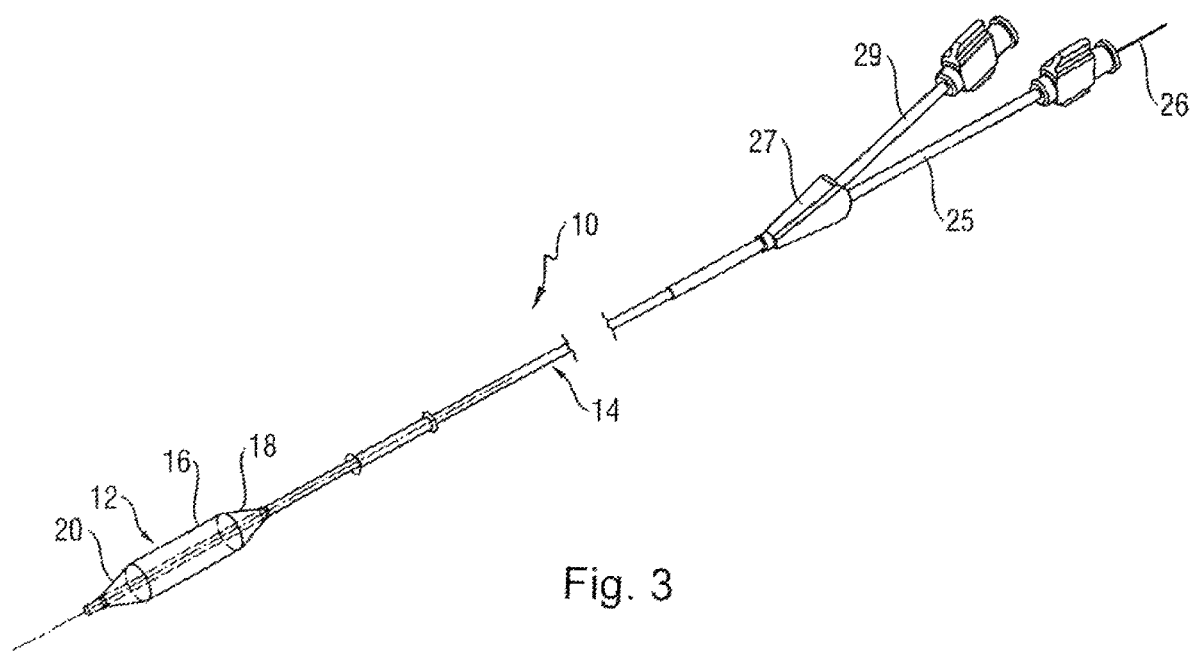
FIG. 3 is a further perspective of the a catheter and balloon according to an embodiment disclosed herein.

Provided is a catheter structure in the form of a tubular catheter 10 capable of being actuated in some manner in order to provide a treatment. In this one example for purposes of illustration, the catheter 10 includes a distal portion 11 with an actuatable element in the form of a balloon 12 mounted on a catheter tube 14. Referring to FIGS. 1, 2, and 3, the balloon 12 has an intermediate section 16, or "barrel" having the working surface W, and end sections 18, 20. In one embodiment, the end sections 18, 20 reduce in diameter to join the intermediate section 16 to the catheter tube 14 (and thus sections 18, 20 are generally termed cones or cone sections). The balloon 12 is sealed to catheter tube 14 at balloon ends (proximal 15a and distal 15b) on the end sections 18, 20 to allow the inflation of the balloon 12 via one or more inflation lumens 17 extending within catheter tube 14 and communicating with the interior of the balloon 12.

Figure 4:
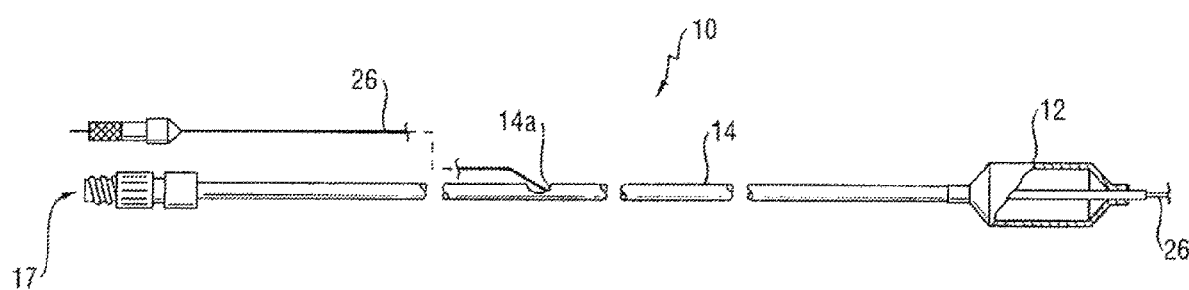
FIG. 4 is an elevational view of a catheter and guidewire according to a further embodiment disclosed herein.

The catheter tube 14 also includes an elongated, tubular shaft 24 forming a lumen 23 that directs another catheter structure, such as guidewire 26, through the catheter 10. As illustrated in FIG. 3, this guidewire 26 may be inserted through a first port 25 of a connector 27, such as a hub, into the lumen 23 to achieve an "over the wire" (OTW) arrangement, but could also be provided in a "rapid exchange" configuration in which the guidewire 26 enters the lumen through a lateral opening 14a closer to the distal end (see FIG. 4). A second port 29 may also be associated with catheter 10, such as by way of connector 27, for introducing a fluid (e.g., saline, a contrast agent, or both) into the interior of the balloon 12 via the inflation lumen 17.

Balloon 12 may include a single or multi-layered balloon wall 28. The balloon 12 may be a non-compliant balloon having a balloon wall 28 that maintains its size and shape in one or more directions when the balloon is inflated. The balloon 12 in such case also has a pre-determined surface area that remains constant during and after inflation, also has a pre-determined length and pre-determined circumference that each, or together, remain constant during and after inflation. However, the balloon 12 could be semi-compliant or compliant instead, depending on the particular use. The catheter 10 may also be adapted for use in connection with resolving chronic total occlusions or artherectomy, and thus may be provided with a cutter or cutting element. The catheter 10 may also be used in connection with a drug, a cutting element, a stent, a graft, or like treatment.

In order to provide an enhanced locatability during an interventional procedure while minimizing the use of fluoroscopy, the catheter 10 may be provided with a marking 30 perceptible along a portion external to the vasculature during the procedure, such as on or along tube 14. As shown in FIG. 5, the marking 30 may comprise a plurality of spaced marks 32, such as circular or partially circular (e.g., 1-359 degrees) bands surrounding the shaft 14 and positioned at pre-determined intervals. These marks 32 may extend from adjacent the connector 27 to the proximal end 15a of the balloon 12, or any portion thereof (which is considered the "proximal portion" of the catheter 10, as contrasted with the distal portion including the balloon 12).

The marks 32 may be evenly or unevenly spaced (e.g., the marks may get progressively closer along the length of the shaft 24). The marks 32 may be of a single color, such as for example black as shown in FIG. 5, but as shown in FIG. 6 may also be provided in different shades or colors. The marks 32 may also comprise hash lines with gradations identified by numbers, letters, or symbols and, thus, may effectively form a ruler. In any case, the marks 32 may be non-radiopaque or otherwise may not be adapted to fluoresce.

The marking 30 may also comprise a biocompatible chemiluminescent or photoluminescent material that may be easily viewed in the low light conditions often present during a procedure involving fluoroscopy. Alternatively or additionally, the marking 30 may be provided in a manner that allows for tactile perception, such as in the forms of notches, bumps, ridges, recesses, or like structures that can be counted even when not directly visible. In any case, the marking 30 may be incorporated directly into the material of the tube 14 or placed thereon (including possibly by using printing techniques).

Figure 7:
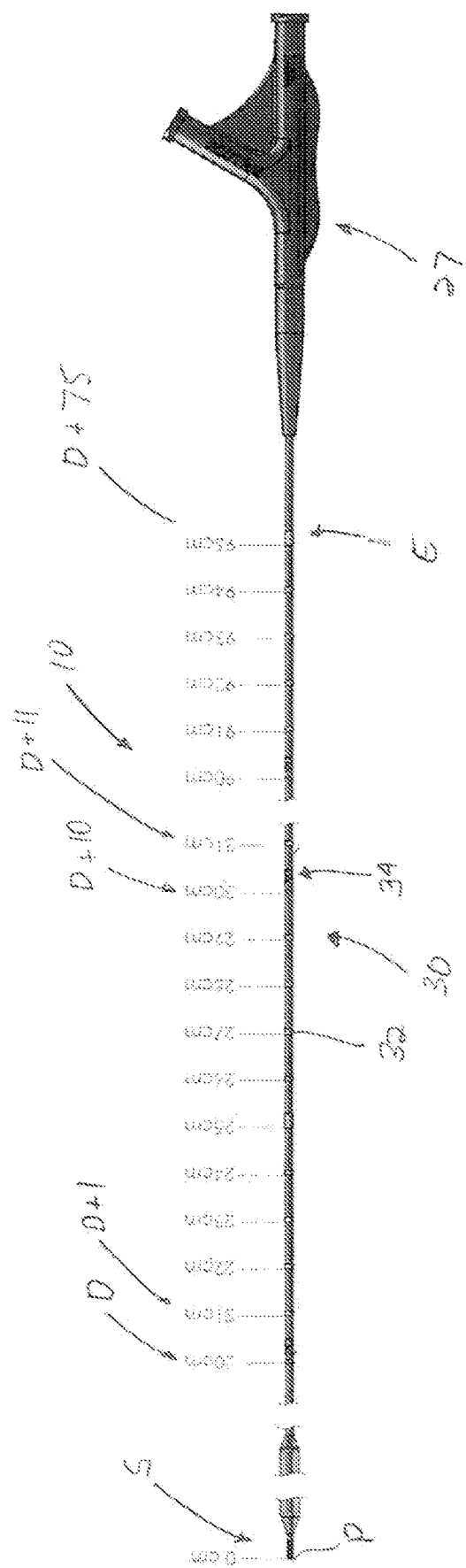
FIG. 7 shows details of a catheter structure according to a further embodiment of the present disclosure.

A further embodiment is shown in FIG. 7. In this embodiment, it can be understood that the marking 30 is provided on the catheter 10 in the form of spaced marks 32, each of which represents a known distance from a pre-determined, fixed location on the catheter 10. In this one illustrated example, the fixed location is the distal tip P, which thus may be considered the starting point S in terms of the measured distance (but the starting point S could be located elsewhere on a structure connected to the catheter 10, such as at the balloon distal end 15b, along the body of the balloon 12, or at the balloon proximal end 15a, as non-limiting examples). Each mark 32 may then represent a fixed distance in from the starting point S, such as mark 32 at point D indicating a distance of 20 centimeters (which is simply an exemplary value). Point D+1 represents a further distance, such as 21 centimeters, in a known increment (which could be centimeters, but could also be millimeters, meters, inches, feet, etc. or portions thereof—the particular units are not considered to be important). The marks 32 may be provided up to a pre-determined end point E, such as D+75 from the starting point S, which in this case represents 95 centimeters (but again, may be any value depending on the desired scale, catheter length, procedure, etc.).

Optionally, the catheter 10 may also be provided with one or more secondary markings 34 in the form of printed indicia representative of distance, such as in the form of alphanumeric characters. For example, between marking D+10 and marking D+11 in the illustrated embodiment, the number "30" may be printed on the shaft as an indication of the distance from the zero point Z, which here is thirty centimeters (but again is simply an example). This allows the clinician to assess the value for adjacent marks 32 quickly, even when provided in a form that does not admit to being perceptable as a particular distance (e.g., a band). The use of characters (e.g., X=10 cm, L=50, C=100) is also possible to determine the distance, as is the use of a key in connection therewith (e.g., A=10 cm, B=50 cm, C=100 cm).

Figure 8:
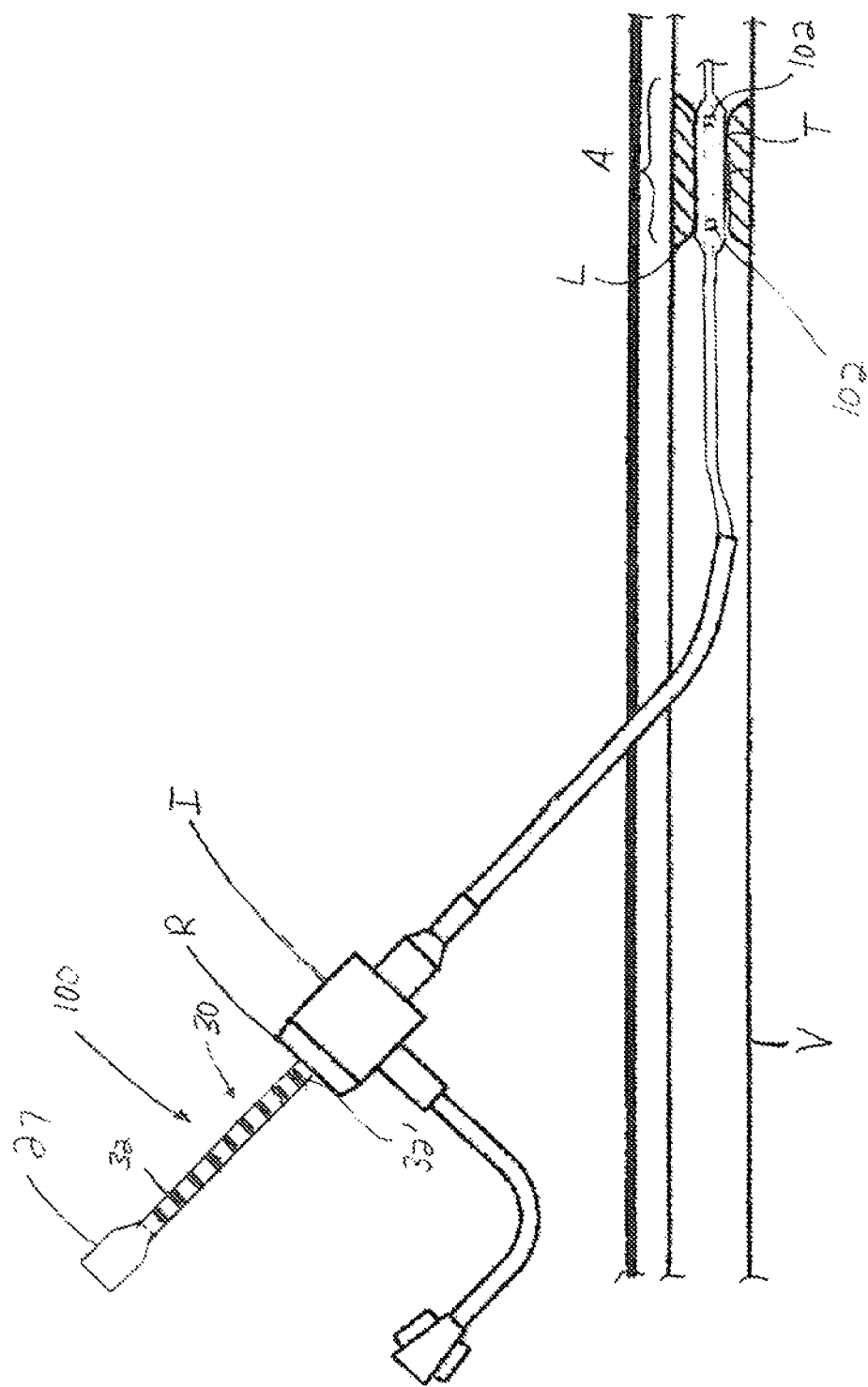
FIG. 8 shows one way of using a catheter structure according to an embodiment of the present disclosure.

In use, and with reference to FIG. 8, a catheter 100 including the marking 30 may be inserted in to a vessel V to a particular treatment area A, which is shown as comprising a lesion L but may take other forms (e.g, a chronic total occlusion, or a location at which the application of a stent, graft, or the like, is desired). This may be done following an assessment of the location of the treatment area, such as by performing a diagnostic angiogram. Inserting the catheter 100 may involve viewing the passing marks 32 during insertion through the introducer I, and either counting them or stopping the insertion process when a known distance is reached. At the point where the marking 30 (such as mark 32') corresponds to the intended distance of insertion, the clinician is assured that the treatment area A has been reached by the distal portion of the catheter 10 (especially when the tip P reflects the starting point S, in which case the known length of the lesion L and the known length of the balloon 12 or other treatment may be used to achieve proper positioning using simple math). Radiopaque markers, such as bands 102, may optionally be provided to aid in confirming the location using fluoroscopy, the use of which has otherwise been minimized as the result of using the marking 30 to position the catheter 100.

Figure 9:
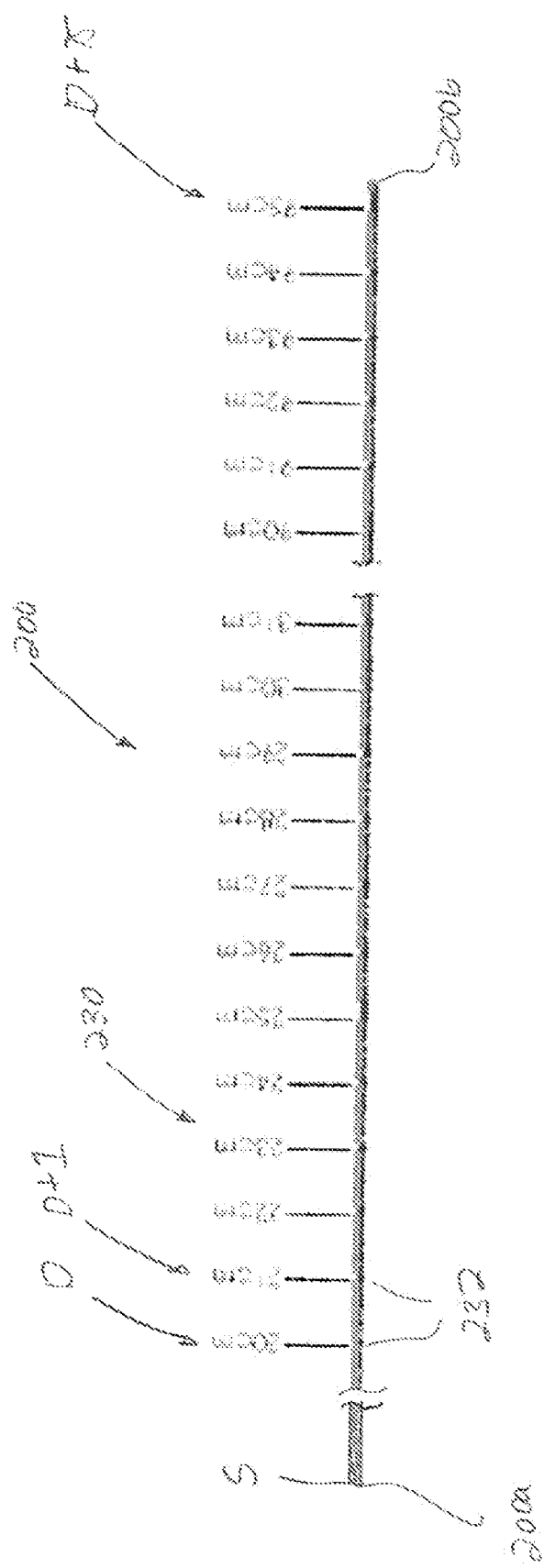
FIG. 9 shows details of a catheter structure in the form of a guidewire according to another aspect of the disclosure.

An alternative aspect of the disclosure is to provide a catheter structure in the form of a guidewire 200 with a marking 230, which may be along a portion external to the body during the procedure. As shown in FIG. 9, the marking 230 may comprise a plurality of spaced marks 232, such as bands. These marks 232 may extend from adjacent a distal end 200a of the guidewire 200 to a proximal end 200b, or any portion thereof.

The marks 232 may be evenly or unevenly spaced (e.g., the marks may get progressively closer along the length of the guidewire 200). The marks 232 may be of a single color, such as for example black, or may be provided in different shades or colors. The marks 232 may also comprise hash lines with gradations identified by numbers, letters, or symbols, and thus may effectively form a ruler. The marks 232 may be non-radiopaque or may otherwise not be visible under fluoroscopy.

The marking 230 may also comprise a biocompatible chemiluminescent or photoluminescent material that may be easily viewed in the low light conditions often present during a procedure involving fluoroscopy. Alternatively or additionally, the marking 230 may be provided in a manner that allows for tactile engagement, such as in the forms of notches, bumps, ridges, recesses, or like structures that can be counted even when not directly visible. In any case, the marking 230 may be incorporated into the material of the guidewire 200 or placed thereon (including possibly by using printing techniques).

Each mark 232 may then represent a fixed distance in from the starting point S, such as mark 232 at point B indicating a distance of 20 centimeters (which is simply an exemplary value). Point D+1 represents a further distance, such as 21 centimeters, in a known increment (which could be centimeters, but could also be millimeters, meters, inches, feet, etc. or any divisions thereof—the particular units are not considered to be important). The marks 232 may be provided up to a pre-determined point D+75 from the starting point S, which in this case represents a distance of 95 centimeters (but again, may be any value depending on the desired scale, catheter length, procedure, etc.).

Figure 10:
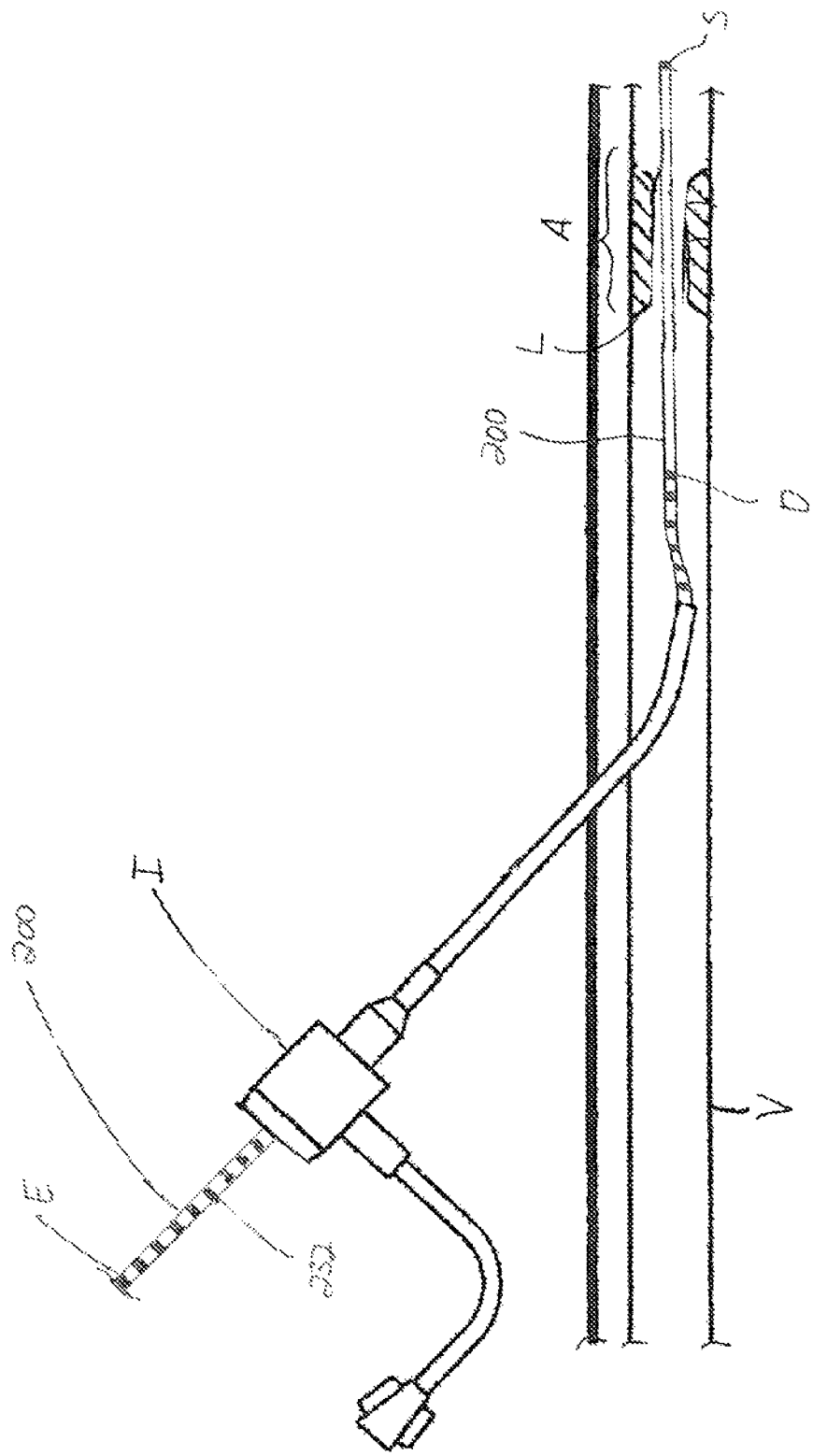
FIG. 10 and FIG. 11 show a way of using the guidewire of FIG. 9 according to an embodiment of the present disclosure.

In use, with reference to FIG. 10, a guidewire 200 including the marking 230 may be inserted in to a vessel V to a particular location, such as adjacent to a treatment area A. This may include a lesion L, as shown, but as noted above may take other forms (e.g, a chronic total occlusion). Prior to the insertion, an assessment of the location of the treatment area, such as by performing a diagnostic angiogram, may be completed.

Inserting the guidewire 200 may involve viewing the passing marks 232 during insertion through the introducer I, and either counting them or stopping the insertion process when a known distance is reached (note references S as starting point, D as a first mark, and E as the end point mark). At the point where the marking 230 (such as mark 232') corresponds to the intended distance of insertion, the clinician is assured that the treatment area A has been reached. In the case where the guidewire 200 includes at least partially radiopaque markers, the location may be confirmed using fluoroscopy, the use of which has otherwise been minimized as the result of using the marking 230 to position the guidewire 200 in the vasculature.

Figure 11:
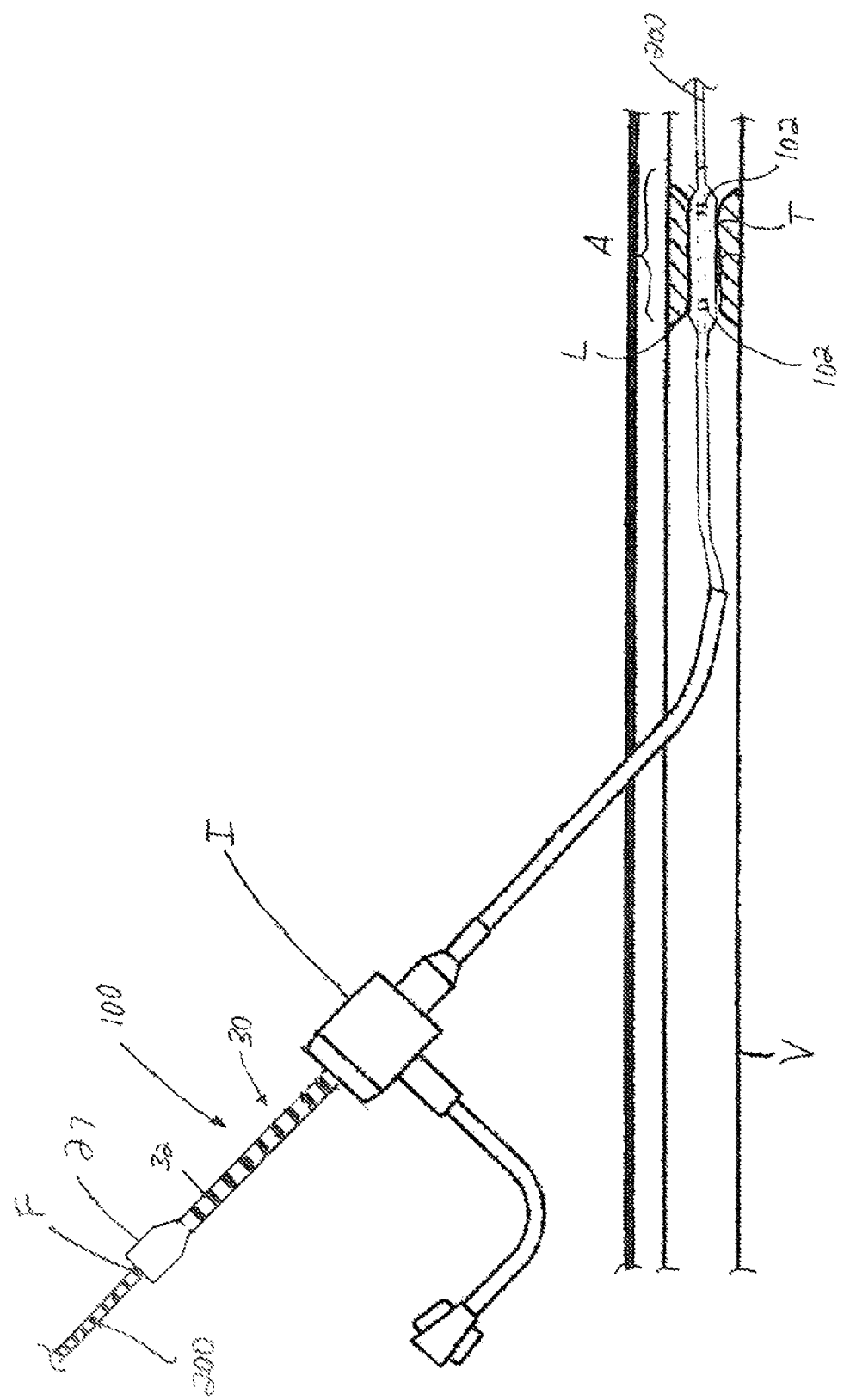

With knowledge of the distance to the treatment area A thus provided by the marking 230 on the guidewire 200, the clinician may choose an appropriate treatment device, such as a catheter (including those examples mentioned here; see catheter 100 in FIG. 11) having a suitable length. The marking 230 may also then be used in positioning the catheter 100 at the treatment area A by using the marks 232 to determine the insertion distance, such as with respect to a reference point F on the guidewire 200 and thereby potentially further reduce the amount of fluoroscopy required.

The technology disclosed herein may be applied to various types of catheters, without limitation. For example, it may be applied to guide catheters, diagnostic catheters, IVUS catheters, OCT catheters, as well as all crossing or thrombectomy catheters (including those using mechanical (e.g., rigid tips, cutters, etc.), laser, fluid, or vibration energy to penetrate through blockages or occlusions). In one particular example, and with reference to FIG. 12, such a crossing catheter 300 may be used to gain access to a desired treatment area A, such as by penetrating through an occlusion O.

Using the marking 330 comprised of marks 332 (which may be the same form as marks 32 or 232) in connection with such a crossing catheter 300, the clinician may note a first mark (such as mark M) on the catheter 300 (such as external to the vasculature) corresponding to the distance of insertion of the catheter at the proximal end or margin X of the treatment area A (which may be relative to an external structure, such as a point on a sheath, introducer I, or the like). Once the crossing catheter 300 is advanced to the end of the treatment area A, such as at the distal end or margin Y of the occlusion O (see FIG. 13), a second mark 332 (such as mark N) on the crossing catheter 300 may be noted. The first and second marks M, N together thus define the length of the treatment area A, and can be measured external to the vasculature in for developing the treatment plan or otherwise.

Subsequently, a second catheter 400 with a marking 430 comprising corresponding or matching marks 432 (such as, for example, a catheter including artherectomy technology (e.g., any of orbital, rotational, laser, and directional devices), thrombectomy technology, PTA technology, stent technology, or any other technology) may be inserted the precise distance necessary to place the corresponding portion of the catheter 400 for providing the particular treatment at a location corresponding to the treatment area A. This may be achieved by noting the relative location of the corresponding marks (such as M, N, which as noted above may be color coded, specially arranged or shaped, identified by an alphanumeric indicator (such as to form a ruler)) or otherwise indicated to correspond to the marks 332 on the crossing catheter 300). In the illustrated embodiment, the technology is a PTA technology including treatment T in the form of an inflatable balloon and an associated guidewire 200 passing through the opening in the occlusion O formed using the crossing catheter 300, but as noted could take other forms.

As should be appreciated, this process can be done repeatedly using different types of catheters for different uses, but having matching marking technology, all without the prolonged use of fluoroscopy in order to determine whether the treatment area A has been reached and the associated time involvement. The overall length of the procedure may this be reduced, which is especially beneficial since patients requiring the most serious interventions (e.g., CTOs) are usually the least able to tolerate lengthy procedures.

As can be further appreciated, the crossing catheter 300 and second catheter 400 may be provided as a kit. This arrangement would aid the clinician in assuring that the marks are precisely matched, which may of course be done during the manufacturing process.

While the disclosure presents certain embodiments to illustrate the inventive concepts, numerous modifications, alterations, and changes to the described embodiments are possible without departing from the sphere and scope, as defined in the appended claims. For example, any ranges and numerical values provided in the various embodiments are subject to variation due to tolerances, due to variations in environmental factors and material quality, and due to modifications of the structure and shape of the balloon, and thus can be considered to be approximate and the term "approximately" means that the relevant value can, at minimum, vary because of such factors. Also, the drawings, while illustrating the inventive concepts, are not to scale, and should not be limited to any particular sizes or dimensions. Accordingly, it is intended that the present disclosure not be limited to the described embodiments, but that it has the full scope defined by the language of the following claims, and equivalents thereof.

The invention claimed is:

1. A kit for treating a treatment area in a vasculature of a patient, comprising:
   a guidewire having a first distal portion adapted for positioning at or near the treatment area and a first proximal portion including a plurality of first markings perceptible by the clinician external to the vasculature without the use of fluoroscopy, each of the plurality of first markings being representative of a length from a first predetermined starting point on the guidewire; and
   a catheter having a shaft including a second distal portion adapted for positioning at the treatment area and a second proximal portion, the second proximal portion including a plurality of second markings perceptible by the clinician external to the vasculature without the use of fluoroscopy, each of the plurality of second markings comprising circular bands surrounding the shaft, and said plurality of second markings being representative of a length from a second predetermined starting point of the catheter;
   wherein a distance between the first predetermined starting point and each of the first markings corresponds to a distance between the second predetermined starting point and each of the second markings; and
   wherein the catheter comprises a balloon.

2. The kit according to claim 1, wherein the balloon is located at a distal end of the catheter, and the second predetermined starting point is located at a proximal end or a distal end of the balloon.

3. The kit according to claim 1, further including a radiopaque marker adjacent the balloon.

4. The kit according to claim 1, wherein the plurality of first markings are spaced at regular intervals.

5. The kit according to of claim 1, wherein each of the guidewire and the catheter further includes alphanumeric markings corresponding to at least one of the plurality of first markings and at least one of the plurality of second markings.

6. The kit according to claim 1, wherein at least one of the plurality of first markings or the plurality of second markings is chemiluminescent or photoluminescent.

7. The kit according to claim 1, wherein the plurality of first markings comprise spaced bands.

8. The kit according to claim 1, wherein the catheter comprises a treatment element selected from the group consisting of a drug, a stent, a graft, a cutter, a focused force wire, or any combination thereof.

9. The kit according to claim 1, wherein the catheter includes a technology selected from the group consisting of an artherectomy technology, a thrombectomy technology, a PTA technology, a stent technology, and any combination of the foregoing.

* * * * *